(12) United States Patent
Glick et al.

(10) Patent No.: US 10,881,505 B2
(45) Date of Patent: Jan. 5, 2021

(54) OPHTHALMOSURGICAL INJECTOR SYSTEM

(71) Applicant: Carl Zeiss Meditec Production, LLC, Ontario, CA (US)

(72) Inventors: Robert Glick, Trabuco Canyon, CA (US); Vincent Sunio, Azusa, CA (US)

(73) Assignee: Cad Zeiss Meditec Production, LLC, Ontario (CA)

( * ) Notice: Subject to any disclaimer, the term of this patent is extended or adjusted under 35 U.S.C. 154(b) by 91 days.

(21) Appl. No.: 15/851,409

(22) Filed: Dec. 21, 2017

(65) Prior Publication Data

US 2019/0192283 A1  Jun. 27, 2019

(51) Int. Cl.
*A61F 2/16* (2006.01)
*A61L 31/04* (2006.01)

(52) U.S. Cl.
CPC ............ *A61F 2/167* (2013.01); *A61F 2/1678* (2013.01); *A61L 31/048* (2013.01); *A61F 2002/16905* (2015.04); *A61F 2002/169053* (2015.04); *A61L 2430/16* (2013.01)

(58) Field of Classification Search
CPC ...... A61F 2/167; A61F 2/1664; A61F 2/1678; A61F 2/1691; A61F 2002/16905; A61F 2002/169053; A61F 2/1613; A61F 2/1629; A61F 2/1662; A61F 2/1667
See application file for complete search history.

(56) References Cited

U.S. PATENT DOCUMENTS

| 5,653,753 | A  | * | 8/1997 | Brady | A61F 2/1664 |
| | | | | | 606/107 |
| 6,406,494 | B1 | * | 6/2002 | Laguette | A61F 2/1613 |
| | | | | | 623/6.37 |
| 2003/0176870 | A1 | * | 9/2003 | Ott | A61F 2/167 |
| | | | | | 606/107 |
| 2004/0059343 | A1 | * | 3/2004 | Shearer | A61F 2/1664 |
| | | | | | 606/107 |

(Continued)

FOREIGN PATENT DOCUMENTS

WO  WO-2015112146 A1 * 7/2015

OTHER PUBLICATIONS

PCT ISR for PCT/US18/66719 published Mar. 5, 2019. (Year: 2019).*

*Primary Examiner* — Katherine M Shi

(74) *Attorney, Agent, or Firm* — Falk Ewers; Ewers IP Law PLLC

(57) ABSTRACT

An ophthalmosurgical injector system includes an injector, which has a handpiece, a plunger, and a dispensing device; an intraocular lens, which has an optic body and two C-shaped haptic arms protruding therefrom; and a cartridge, in which the intraocular lens is received. The dispensing device has an inlet opening at the proximal end and an outlet opening at the distal end. When the plunger is moved forward, the intraocular lens is conveyed from the cartridge through the inlet opening to the outlet opening of the dispensing device. When the intraocular lens is held in the cartridge in a compressed and preloaded state, a subregion of each of the haptic arms bears on and covers the optic (Continued)

body. In a plan view, the optic body of the preloaded intraocular lens has a circular surface area with a diameter of at least 4.0 mm that is not covered by the haptic arms.

4 Claims, 3 Drawing Sheets

(56) References Cited

U.S. PATENT DOCUMENTS

| | | | | |
|---|---|---|---|---|
| 2005/0033308 A1* | 2/2005 | Callahan | ............... | A61F 2/1691 |
| | | | | 606/107 |
| 2009/0036898 A1* | 2/2009 | Ichinohe | ............... | A61F 2/1678 |
| | | | | 606/107 |
| 2015/0320549 A1* | 11/2015 | Cole | ..................... | A61F 2/1664 |
| | | | | 606/107 |

* cited by examiner

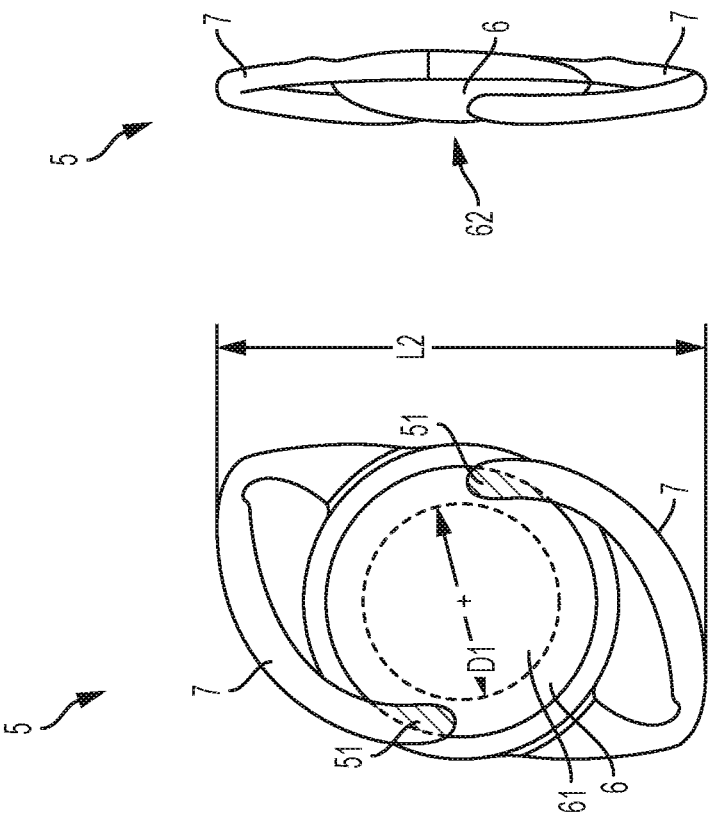
FIG. 4
FIG. 3
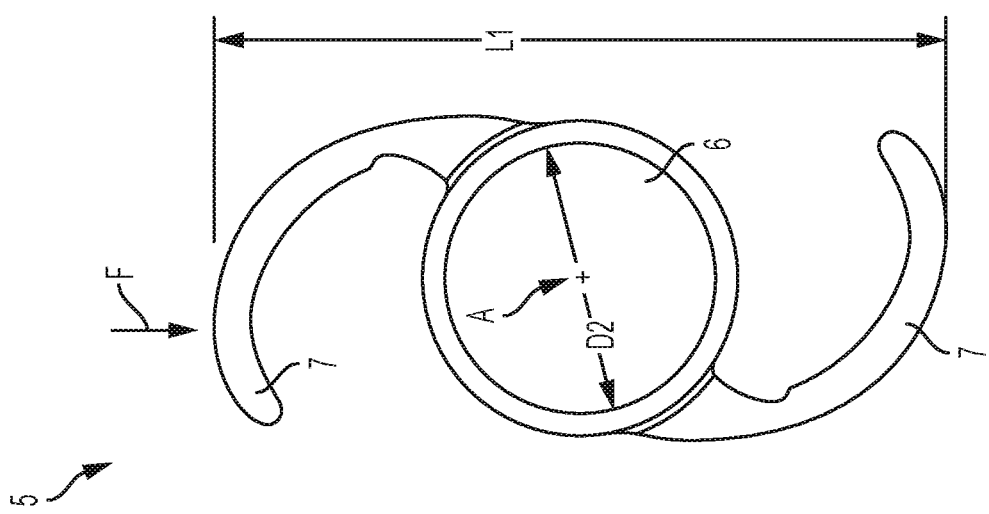
FIG. 2

OPHTHALMOSURGICAL INJECTOR SYSTEM

FIELD OF THE DISCLOSURE

The disclosure relates to an ophthalmosurgical injector system, which has an injector, an intraocular lens, and a cartridge.

BACKGROUND

In clouding of the lens of the human eye, referred to in medicine as cataract, it may be medically necessary to remove the clouded lens from the capsular bag. A method commonly used for this purpose is phacoemulsification of the lens, in which the clouded lens of a patient is emulsified into small particles by means of ultrasound and aspirated. The surgeon then inserts an artificial intraocular lens into the then lens-free capsular bag.

For this purpose, a surgeon can use an injector system, which has an injector. The injector has a handpiece and a plunger which is guided in the handpiece and is longitudinally movable therein. In addition, the injector has an intraocular lens, which has an optic body. The intraocular lens can have two C-shaped haptic arms which protrude from the optic body and are arranged lying opposite each other. The haptic arms serve to come into contact with the inner wall of the capsular bag and to orient the optic body centrally within the capsular bag, such that better vision can be restored to the patient.

The injector system moreover has a cartridge, in which the intraocular lens is received, wherein the cartridge is inserted in the injector. In addition to the handpiece and the plunger, the injector has a dispensing device, wherein the dispensing device has an inlet portion that leads to a distal outlet opening of the dispensing device, wherein the intraocular lens, by means of a forward movement of the plunger, can be conveyed from the cartridge through the dispensing device in the direction of the outlet opening. During the operation, the surgeon uses the injector by pushing the outlet opening of the injector through the cornea of the eye as far as the capsular bag. Then, with an increasing forward movement of the plunger, the surgeon ensures that the intraocular lens is inserted through the dispensing device and from there into the capsular bag. The intraocular lens unfolds in the capsular bag in such a way that the haptic arms come to bear on the inner wall of the capsular bag and, in this way, the optic body is oriented centrally within the capsular bag.

The intraocular lens is initially in an untensioned or unloaded state in the cartridge. The distance from one haptic arm to the other haptic arm is ca. 12 mm in the unloaded state. When an operation is pending, the plunger is pushed into the handpiece immediately prior to the operation and thus moved forward such that the haptic arms are moved closer to the optic body. The intraocular lens is then in a compressed state. Since the haptic arms are coupled with the optic body by means of a very elastic hinge joint, only a relatively slight force is needed to move the haptic arms onto the optic body. There is then a danger of the plunger being moved too far forward and of the intraocular lens thereby reaching the dispensing device. Then it is possible that there is only a relatively small distance until the intraocular lens arrives at the distal end of the dispensing device. This situation is uncomfortable for a surgeon because it results in an uncertainty concerning the handling of the injector system.

SUMMARY

It is an object of the disclosure to make available an ophthalmosurgical injector system with which an intraocular lens, contained in the latter, can be conveyed easily and safely through a dispensing device of the injector system, which injector system is of a compact design.

The ophthalmosurgical injector system has:
an injector, which has a handpiece, a plunger and a dispensing device,
an intraocular lens, which has an optic body and two C-shaped haptic arms protruding from the latter,
a cartridge, in which the intraocular lens is received, wherein the cartridge is inserted in the injector,
 a) wherein the dispensing device has an inlet opening at the proximal end and an outlet opening at the distal end, wherein the intraocular lens, by means of a forward movement of the plunger, can be conveyed from the cartridge through the inlet opening to the outlet opening of the dispensing device,
 b) wherein the intraocular lens is held in the cartridge in a compressed and preloaded state in which a subregion of each of the C-shaped haptic arms bears on the optic body and covers the latter there, and
 c) wherein the optic body of the preloaded intraocular lens has, in a plan view, a circular surface area not covered by the haptic arms, which circular surface area has a diameter of at least 4.0 mm.

It was hitherto assumed that a haptic arm should absolutely be prevented from bearing on the optic body for a prolonged period. The reason for this is that a haptic arm may adhere on the top surface of the optic body and that after implantation of the intraocular lens into the capsular bag the intraocular lens is no longer able to move back in its original position by itself.

The inventors have now found, however, that the intraocular lens may be held and stored in a compressed and preloaded state in which a subregion of each of the C-shaped haptic arms can be allowed to bear on the optic body and partially cover the latter there. It is important that the optic body of the preloaded intraocular lens has, in a plan view, a circular surface area which is not covered by the haptic arms and which has a diameter of at least 4.0 mm.

This has the effect that the haptic arms of the intraocular lens may remain during a long period, possibly several years, in a preloaded state wherein after an implantation of the intraocular lens into the capsular bag the haptic arms move reliably back in its original position. The bending of the haptic arms such that the circular surface area having a diameter of at least 4.0 mm is not covered by the haptic arms is advantageous because a hinge joint between the optic body and corresponding haptic arm suffers no plastic deformation, but only an elastic deformation. Should an adhesion between optic body and haptic arm occur, then the elastic restoration force of the haptic arm is sufficient to release the haptic arm from the optic body. In addition, the intraocular lens is situated in a predetermined position in the injector system during a storage period so that the surgeon, prior to start of the implantation, can properly estimate the distance until the intraocular lens will reach the distal end of the dispensing device.

Furthermore, there is an additional advantage: By means of preloading of the haptic arms according to the disclosure in that the optic body of the intraocular lens has, in a plan view, a circular surface area not covered by the haptic arms, which circular surface area has a diameter of at least 4.0 mm, the haptic arms cannot damage (e.g., by scratching) the uncovered circular surface area. Such a damage may then only occur at the periphery of the circular surface area e.g., during transportation of the preloaded intraocular lens. However, such damage is not significant and is acceptable because the diameter of a capsulorhexis is usually only 4.0 mm at most. Thus, damage of the optic body in a region which adjoins the circular surface area, and in which a haptic arm bears on the optic body, does not have a negative impact on a patient in terms of the quality of vision.

A further advantage of the injector system is that the intraocular lens can remain in the compressed and preloaded state in the cartridge. This step, in which the plunger is moved such that a subregion of each of the C-shaped haptic arms bears on the optic body and covers the latter there, can already be carried out by the manufacturer of the injector system at the time of production of the injector system, such that the surgeon or an assistant to the surgeon no longer has to do this immediately prior to the start of an operation. There is then also no longer any danger of the haptic arms accidentally being moved too far onto the optic body. Instead, immediately prior to the operation, the surgeon simply has to add a viscoelastic to the cartridge and fold or roll up the intraocular lens. He can then immediately begin conveying the intraocular lens through the dispensing device. During this movement of the plunger, the force that has to be applied is relatively constant. The surgeon no longer has to apply the very slight force for compressing the haptic arms, and therefore the surgeon no longer has to take into account a considerable difference between the forces that are to be applied during the movement of the plunger. Overall, this means that the intraocular lens can be easily and safely conveyed through the dispensing device of the injector system by the surgeon.

In addition, the injector system according to the disclosure allows the length of the injector to be kept relatively short. The intraocular lens, which in the unloaded state has a length of approximately 12 mm from one haptic arm to the other haptic arm, is much shorter in the compressed and preloaded state. The injector system can thus be produced and supplied in a more compact form.

The injector system preferably has a locking device with which the plunger can be locked in a fixed position relative to the handpiece or to the cartridge. In this way, the intraocular lens can be easily maintained, stored, and transported in a compressed and preloaded state. The locking device is preferably a mechanical latching element, for example a ratchet, which inhibits or blocks the plunger only in a rearward direction. The locking device can come into engagement only with the handpiece or only with the cartridge or in combination with the handpiece and with the cartridge. If the locking device connects the plunger to the cartridge, locking can take place in direct proximity to the intraocular lens. Thus, during what may be a long period of storage of the injector system, the intraocular lens can be preloaded in a secure and stable manner.

According to an exemplary embodiment of the disclosure, the cartridge has wing elements coupled to hinges, such that, in an opened position of the wing elements, the insertion of the intraocular lens into the cartridge is permitted and, by pivoting the wing elements to a closed position, the folding of the inserted intraocular lens is permitted. The pivoting of wing elements to a closed position can be performed very easily by a surgeon, and no forward movement of a plunger is needed to achieve folding of the intraocular lens.

The external diameter of the compressed and preloaded intraocular lens is preferably at most 8 mm. This permits a particularly compact injector system.

The intraocular lens is preferably made of a hydrophobic acrylic polymer. This permits compression, preloading and storage of the intraocular lens over several years, after which the intraocular lens, when inserted into a capsular bag, nevertheless is able to unfold into an unloaded state.

BRIEF DESCRIPTION OF THE DRAWINGS

Further advantages and features of the disclosure are explained with reference to the following drawings, in which:

FIG. 2 shows a schematic illustration of an artificial intraocular lens in the unloaded state, in a plan view;

FIG. 3 shows a schematic illustration of the artificial intraocular lens in the compressed state, in a plan view;

FIG. 4 shows a schematic illustration of the artificial intraocular lens in the compressed state, in a side view.

DETAILED DESCRIPTION OF EXEMPLARY EMBODIMENTS

Figure 1:
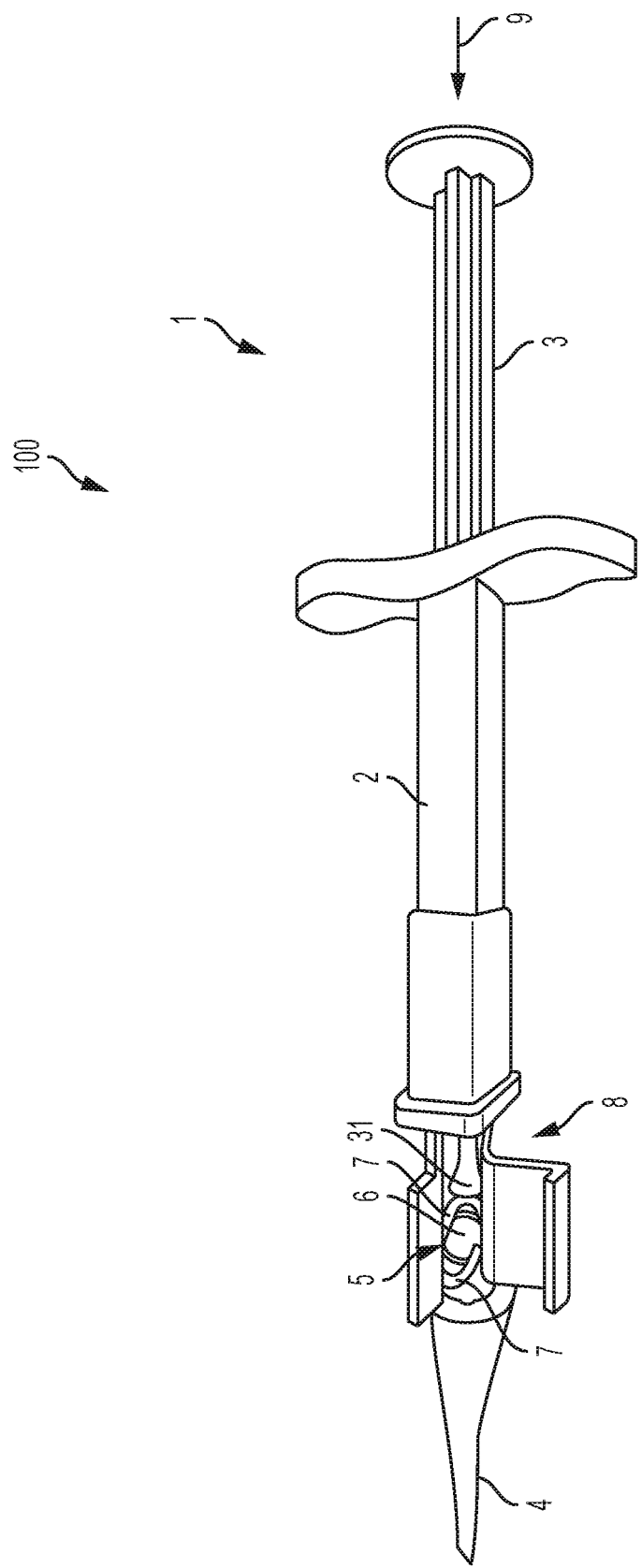
FIG. 1 shows a schematic illustration of an injector system.

FIG. 1 shows a schematic illustration of one exemplary embodiment of an ophthalmosurgical injector system 100 according to the disclosure. The injector system 100 has an injector 1, which has a handpiece 2 and a plunger 3. In addition, the injector has a dispensing device 4 through which an artificial intraocular lens 5 can be conveyed. The intraocular lens 5 has an optic body 6 and two C-shaped haptic arms 7 which protrude therefrom and are arranged lying opposite each other (see also FIG. 2). The intraocular lens 5 is inserted in a cartridge 8, which is positioned in the injector system 100 before the dispensing device 4. By means of a forward movement (see arrow 9), the plunger 3 guided in the handpiece 2 can have its distal end 31 come into contact with one of the haptic arms 7, whereupon the haptic arms 7 deform in the direction toward the optic body 6.

The intraocular lens is, in an unloaded state at the time of production, such that the distance from one haptic arm 7 to the opposite haptic arm 7 has a length L1 (see FIG. 2). When the distal end 31 of the plunger 3 applies a force F to the haptic arms 7 perpendicular to an optical axis A of the optic body 6, the haptic arms reach in the direction of the optic body 6 on account of the elasticity of the material of the intraocular lens, which material is preferably a hydrophobic acrylic polymer.

FIG. 3 shows the intraocular lens 5 in a compressed state, in which a subregion 51 of each of the haptic arms 7 bears on the optic body 6 and partially covers the latter there. The optic body 6 of the preloaded intraocular lens 5 has, in a plan view, a circular surface area 61 not covered by the haptic arms 7, which circular surface area 61 has a diameter D1 of at least 4.0 mm. The outer circumference of the circular surface area is shown by a dotted line in FIG. 3. In this compressed state of the intraocular lens 5, the distance from one haptic arm 7 to the opposite haptic arm 7 has a length L2, which is shorter than the length L1. With a length L1 of 12 mm, such compression of the intraocular lens 5 leads to a length L2 of approximately 7.5 mm to 8 mm. The subregion 51 is a surface representing part of a circular ring which is formed between a ring with the external diameter D2 of the optic body 6 and a ring with the diameter D1 of the circular surface area 61.

FIG. 4 shows the compressed intraocular lens 5 in a side view. It can be seen from this view that a subregion of each of the haptic arms 7 bears on the optic body 6. The haptic arms 7 protrude only slightly, or indeed not at all, above the summit 62 of the optic body 6; this depends on the refractive power of the optic body.

Figure 5:
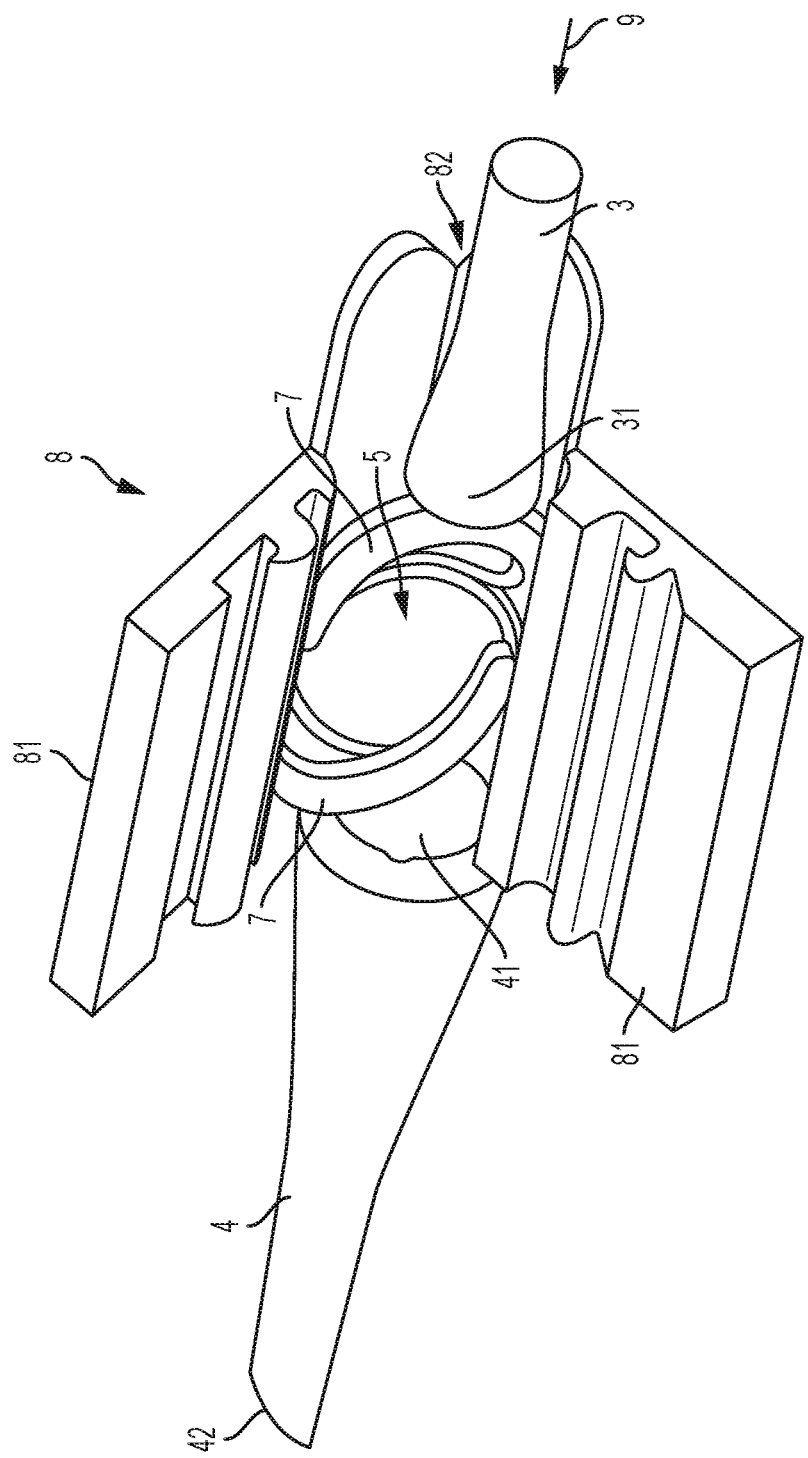
FIG. 5 shows a schematic perspective illustration of a cartridge with wing elements and an intraocular lens inserted into the cartridge and compressed.

FIG. 5 shows a perspective view of the intraocular lens 5 inserted in the cartridge 8 and compressed. The distal end 31 of the plunger 3 is in touching contact with one of the haptic arms 7. The cartridge 8 has two wing elements 81 arranged on two parallel walls of the cartridge 8, which are shown in an opened position in FIG. 5. The cartridge 8 includes generally parallel interior walls and is configured to receive the intraocular lens and to be inserted in the injector such that the intraocular lens is in any position in the cartridge in a compressed and preloaded state in which a subregion of each of the C-shaped haptic arms bears on the optic body and covers the optic body in the subregion when the cartridge is closed, as shown in FIG. 5. By pivoting the wing elements 81 about an associated hinge 82, preferably a film hinge, the intraocular lens 5 can be folded or rolled up, such that it can be pushed into an inlet portion 41 of the dispensing device 4. By continued movement of the plunger 3 in the direction of the arrow 9, the intraocular lens 5 emerges at the distal end of the dispensing device 4, i.e., at the outlet opening 42, to be introduced into the capsular bag of an eye.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. An ophthalmosurgical injector system comprising:
    an injector having:
        a handpiece,
        a plunger, and
        a dispensing device,
    an intraocular lens having an optic body and two C-shaped haptic arms protruding from the optic body, and
    a cartridge comprising generally parallel interior walls and being configured to receive the intraocular lens and to be inserted in the injector such that the intraocular lens is in any position in the cartridge in a compressed and preloaded state in which a subregion of each of the C-shaped haptic arms bears on the optic body and covers the optic body in the subregion when the cartridge is closed,
    wherein the dispensing device has an inlet opening at a proximal end and an outlet opening at a distal end thereof,
    wherein the dispensing device is configured to convey the intraocular lens from the cartridge through the inlet opening to the outlet opening of the dispensing device when the plunger is moved forward, and
    wherein the optic body of the intraocular lens in the preloaded state has, in a plan view, a circular surface area not covered by the haptic arms, which circular surface area has a diameter of at least 4.0 mm.

2. The ophthalmosurgical injector system as claimed in claim 1, the cartridge further comprising:
    wing elements coupled to a hinge,
    wherein an insertion of the intraocular lens into the cartridge is permitted when the wing elements are in an opened position, and,
    wherein folding of the inserted intraocular lens is permitted when the wing elements are pivoted to a closed position.

3. The ophthalmosurgical injector system as claimed in claim 1, wherein an external diameter of the compressed and preloaded intraocular lens is at most 8 mm.

4. The ophthalmosurgical injector system as claimed in claim 1, wherein the intraocular lens is made of a hydrophobic acrylic polymer.

\* \* \* \* \*